United States Patent [19]
Levings, III et al.

[11] Patent Number: 5,807,998
[45] Date of Patent: Sep. 15, 1998

[54] MODIFIED URF13-T PROTEIN

[75] Inventors: Charles S. Levings, III, Raleigh, N.C.; Ralph E. Dewey, Metuchen, N.J.; Carl J. Braun, Raleigh, N.C.

[73] Assignees: Mycogen Plant Science, Inc., San Diego, Calif.; North Carolina State University, Raleigh, N.C.

[21] Appl. No.: 426,313

[22] Filed: Apr. 21, 1995

Related U.S. Application Data

[62] Division of Ser. No. 58,052, May 5, 1993, Pat. No. 5,409,837, which is a continuation of Ser. No. 342,119, Apr. 24, 1989, abandoned, which is a continuation-in-part of Ser. No. 144,557, Jan. 14, 1988, abandoned.

[51] Int. Cl.⁶ .......................... C07K 14/00; C12N 15/85
[52] U.S. Cl. ...................... 530/376; 530/402; 435/252.3
[58] Field of Search .................................. 530/402, 376; 435/252.3

[56] References Cited

PUBLICATIONS

Dewey, R.E., C.S. Levings III, D.H. Timothy (1986) "Novel Recombinations in the Maize Mitochondiral Genome Produce a Unique Transcriptional Unit in the Texas Male–Sterile Cytoplasm" Cell 44:439–449.

Dewey, R.E., D.H. Timothy, C.S. Levings III (1987) "A mitocondrial protein associated with cytoplasmic male sterility in the T cytoplasm of maize" Proc. Natl. Acad. Sci. USA 84:5374–5378.

Wise, R.P., D.R. Pring. B.G. Gengenbach (1987) "Mutation to male fertility and toxin insensitivity in Texas (T)–cytoplasm maize is associated with a frameshift in a mitochondiral open reading frame" Proc. Natl. Acad. Sci. USA 84:2858–2862.

Forde, B.G., C.J. Leaver (1980) "Nuclear and cytoplasmic genes controlling synthesis of variant mitochondrial polypeptides in male–sterile maize" Proc. Natl. Acad. Sci. USA 77:418–422.

Umbeck, P.F., B.G. Gengenbach (1983) "Reversion of Male–Sterile T–Cytoplasm Maize to Male Fertility in Tissue Culture" Crop Science 23:584–588.

Braun, C.J., J.N. Siedow, C.S. Levings III (1989) "The T–urf13 Gene is Responsible for Toxin Sensitivity in Maize and *E.Coli*" The Molecular Basis of Plant Development, pp. 79–85.

*Primary Examiner*—Lila Feisee
*Assistant Examiner*—Geetha P. Bansal
*Attorney, Agent, or Firm*—Saliwanchik, Lloyd & Saliwanchik

[57] ABSTRACT

A protein and gene encoding it are disclosed which confer sensitivity to *B. maydis* T toxin and the insecticide methomyl, in cells carrying the gene and expressing the protein. Toxin sensitivity domains of the protein have been identified wherein a modification yields a toxin-insensitive product.

8 Claims, No Drawings

MODIFIED URF13-T PROTEIN

INTRODUCTION

This application is a division of U.S. patent application Ser. No. 08/058,052 filed May 5, 1993 (U.S. Pat. No. 5,409,837) which is a continuation of Ser. No. 07/342,119 filed Apr. 24, 1989, now abandoned, which is a continuation-in-part of Ser. No. 07/144,557 filed Jan. 14, 1988, now abandoned.

The invention relates to plant pathology, especially to cytoplasmic male sterility (cms) in maize and to pathotoxin specificity in certain cms maize lines.

BACKGROUND AND PRIOR ART

Maize (*Zea mays* L.) plants carrying the Texas male-sterile cytoplasm (cms-T) are particularly susceptible to the fungal pathogen Bipolaris (Helminthosporium) maydis, race T, the causative agent of Southern Corn Leaf Blight (Hooker, A. L. et al. (1970) Plant Dis. Rep. 54:708). A host-specific pathotoxin (BmT-toxin) isolated from the fungus specifically alters membrane permeabilities of mitochondria from cms-T maize. For structure of BmT and related toxins, see Frantzen. K. A. et al. (1987) Plant Physiol. 83:863. The carbamate insecticide, methomyl, although structurally unrelated, mimics the BmT-toxin effects (Humaydan, H. S. and Scott, E. W. (1977) Hortic. Sci. 12:312). For structure of methomyl and analogs toxic to cms-T maize mitochondria, see Aranda et al. (1987) Phytochem. 26:1909. Mitochondria from maize plants containing either the S or C male-sterile or normal (male-fertile) cytoplasms are unaffected by the BmT-toxin or methomyl. The site of toxin and methomyl action is believed to be at the inner mitochondrial membrane. In response to BmT-toxin or methomyl, cms-T mitochondria exhibit rapid swelling, uncoupling of oxidative phosphorylation, inhibition of malate-driven respiration and leakage of small molecules such as $NAD^+$ and $Ca^{++}$ (Miller, R. J. and Koeppe, D. E. (1971) Science 173:67; Koeppe, D. E. et al. (1978) 201:1227; Berville, A. et al. (1984) Plant Physiol. 76:508; Klein, R. R. and Koeppe, D. E. (1985) Plant Physiol. 77:912; Holden, M. J. and Sze, H. (1984) Plant Physiol. 75:235).

A strict correlation exists between susceptibility to the *B. maydis* pathotoxin and the cytoplasmic male-sterility (cms) trait in maize plants containing the T cytoplasm. Both traits are maternally inherited and attempts to separate the two effects have been unsuccessful. Regeneration of cms-T maize callus from tissue cultures both with and without BmT-toxin selection has given rise to revertant plants that are not only resistant to the BmT-toxin, but are also male fertile; no stable revertants have been obtained that are male sterile and toxin resistant or male fertile and toxin sensitive (Brettell, R. I. S. et al. (1979) Maydica 24:203; Umbeck, P. F. and Gengenbach, B. G. (1983) Crop Sci. 23:584).

A possible explanation for the simultaneous reversion of the two traits is that a single locus of extranuclear origin encodes both phenotypic alternatives, i.e. male fertility and toxin resistance versus male sterility and susceptibility.

A mitochondrial gene unique to T-cytoplasm of maize has been isolated and characterized (Dewey, R. F. et al. (1986) Cell 44:439). Designated urf13-T, it encodes a 13 kd protein associated with the cms trait. The nuclear fertility restorer gene Rf1 alters the transcript of urf13-T, resulting in a significant decrease in abundance of the 13 kd protein. Also, in cms-T plants that have reverted to male fertility and *B. maydis* resistance, the urf13-T reading frame has been found to be either altered or the gene completely deleted. The urf13-T gene has been sequenced and the amino acid sequence of the protein it encodes has been deduced (Dewey, R. E. et al. (1987) Proc. Natl. Acad. Sci. U.S.A. 84:5374).

Preincubation of cms-T maize mitochondria with dicyclohexylcarbodiimide (DCCD), a reagent that preferentially binds covalently to carboxyl groups in hydrophobic regions of proteins, confers protection against the effects of BmT-toxin (Bouthyette, P-Y. et al. (1985) J. Exp. Bot. 36:511; Holden, M. J. and Sze, H. (1987) in *Plant Mitochondria, Structural, Functional and Physiological Aspects,* A. L. Moore and R. B. Beechey, (eds.) Plenum Press, New York, pp. 305–308). Pretreatment of mitochondria with 4 through 15 $\mu$M DCCD prevents toxin-induced inhibition of malate-dependent oxidation, dissipation of the membrane potential, and leakage of accumulated calcium. Preincubation with the water soluble carbodiimide, 1-ethyl-3-(3-dimethylaminopropyl)-carbodiimide, does not protect cms-T mitochondria from toxin action, suggesting that DCCD modifies a component situated in a hydrophobic environment.

SUMMARY OF THE INVENTION

The invention is based on the discovery that urf13-T can be expressed in a bacterial host and that bacteria transformed by expressing the urf13-T gene are rendered susceptible to BmT toxin and to methomyl. Furthermore, domains of the protein have been identified that are responsible for conferring toxin sensitivity on the host cells. Modification of one or more of these domains abolishes the specific toxic effects of BmT toxin and of methomyl. The findings provide a basis for a simple assay for toxin and a screening method for detecting toxin. Expression of the urf13-T gene in bacteria provides a means for destroying those bacteria, if so desired, at any time, by exposing them to BmT toxin or to methomyl or to any of the toxic analogs thereof. Such a trait can be used, for example, if the bacterial strain has been released into an undesired location, where it can be destroyed without harming other organisms. Risk management of bacteria released into the environment is enhanced by incorporating the urf13-T gene into the released strain. A method is also provided for assessing the effects on toxin sensitivity of specific gene modifications. Modified urf13-T genes can be introduced into plants and expressed to create sterility that is not accompanied by toxin sensitivity. The modified genes and the modified proteins they encode are useful for elucidating the structural domains necessary for producing sterility of male reproductive tissues.

BRIEF DESCRIPTION OF THE SEQUENCES

SEQ ID NO. 1 is a nucleotide sequence useful for providing a procaryotic ribosome binding site for synthetic oligonucleotides.

SEQ ID NO. 2 is a nucleotide sequence useful for providing a procaryotic ribosome binding site for synthetic oligonucleotides.

SEQ ID NO. 3 is the sequence of amino acid nos. 2–11 of urf13.

DETAILED DESCRIPTION OF THE INVENTION

The nucleotide sequence of urf13-T has been published (Dewey, R. E. et al. (1986) Cell 44:439). In higher plant mitochondria, CGG codons are believed to designate tryptophan rather than arginine as predicted by the universal code (Fox, T. D. and Leaver, C. J. (1981) Cell 26:315). urf13-T and pATH13-T contain a single CGG codon, corresponding to amino acid position 87 (Dewey, R. E. et al. (1986) Cell 44:439).

The urf13-T gene can be cloned in a plasmid expression vector and expressed in a microbial host. Surprisingly, the transformed host expressing urf13-T is rendered susceptible to BmT toxin and methomyl, although in the absence of these agents, the host appears to grow normally and respires normally. In the presence of toxin, respiration ($O_2$ consumption) is completely inhibited by toxin. The time required to completely inhibit respiration varies with toxin dose: lower doses of toxin require longer times to inhibit respiration completely. Toxin also causes swelling of spheroplasts of the host organism, reflecting permeabilized membranes. An alternative assay for membrane permeabilization is the monitoring of ion leakage, after exposure to toxin, from cells preloaded with $^{86}Rb$ (a radioactive substitute for $K^+$).

The urf13-T protein is found associated with the microbial membrane. Still more surprising is the fact that specific gene alterations can be made that result in expression of a modified urf13-T protein that no longer confers BmT or methomyl sensitivity to the microbial host expressing it, despite the fact that such alterations do not affect the association of the modified protein with the host membrane. Experiments disclosing these features are described in Examples 1, 2, 3 and 4.

The findings provide a basis for a method of detecting and measuring BmT toxin and other compounds such as methomyl having toxin-like specificity for plants having the T cytoplasm. The method involves culturing a microorganism transformed by and expressing the urf13-T gene, dividing the culture into samples and treating the samples respectively with the material to be tested, a sample of known toxicity and a control known to be nontoxic, and measuring $O_2$ consumption and/or ion leakage in each sample. By comparing the time required to reach a defined level of inhibition for example, complete (100%) inhibition or 50% inhibition, over a range of known toxin concentrations, a standard curve can be developed against which the amount of toxin in the test sample can be quantified. Less than 7.8 ng/ml of BmT toxin can be readily measured. Nonspecific (unrelated to interaction with urf13-T protein) inhibition of respiration of test samples can be corrected for by use of a control test using untransformed cells, grown to approximately the same density. Rates of $^{86}Rb$ leakage from test samples can be compared to rates of leakage from cells transformed with a plasmid that does not contain the urf13-T gene insert. Typically, such control cells show no detectable leakage for at least forty minutes following exposure to toxin or methomyl. These assays may be used qualitatively as a method for screening for BmT toxin in unknown samples. The methods are therefore useful diagnostics to identify the presence of B maydis race T in field samples. Other parameters of the assays can be varied and optimized as desired according to principles understood by those of ordinary skill in the art. In particular, the choice of host microorganism and expression system can influence the sensitivity of the assays. E. coli, used in the example, is very convenient because it is easy and safe to culture and there are many vectors and expression systems available for use with E. coli. Other organisms may present other advantages. The results described herein demonstrate that the urf13-T protein becomes associated with membranes in organisms as diverse as maize and E. coli. In principle, any transformable organism capable of aerobic respiration can serve as host for the urf13-T gene which, if expressed to a sufficient level, will render the organism susceptible to inhibition of respiration and energy-dependent ion uptake by exposure to BmT, methomyl and other compounds having similar toxic specificity.

The urf13-T gene provides a useful "silver bullet" for microorganism strains that must be inactivated swiftly and selectively. Bacteria that express the urf13-T gene introduced into the environment can be selectively destroyed by treatment with methomyl or by application of BmT. Methomyl has been used commercially as an insecticide under the name "Lannate." (a trademark of DuPont, Wilmington, Del.). While these compounds have a nonspecific toxicity at higher doses, both are specifically toxic to microorganisms expressing urf13-T at lower doses. Analogs of methomyl have been found that are of comparable toxicity to BmT (Aranda, G. et al. (1987) Phytochem. 26:1909). For brevity, BmT, methomyl and their analogs having similar toxic specificity will be termed simply "toxin" herein. The ability to selectively inactivate a given microorganism can be used to advantage in laboratory work as well. For example, where an organism is considered hazardous, incorporating expressible urf13-T gene provides a failsafe means of biological containment.

The results described herein provide a method for evaluating the effects on toxin sensitivity of various modifications of the urf13-T gene. As described in Examples 1 and 4, various modified urf13-T genes have been prepared and expressed in a microorganism. Modifications at certain amino acid residues result in loss of toxin sensitivity, while many modifications have no effect. The results demonstrate that specific regions of the urf13-T protein are required for one of its functional properties, the ability to confer toxin sensitivity on organisms that express it. Such specific regions are termed herein toxin sensitivity domains. Modification within a toxin sensitivity domain resulting in loss of toxin sensitivity is termed a sensitivity-loss modification. Modification of the urf13-T gene such that one or more toxin sensitivity domains is deleted or altered in sequence can result, upon expression, in synthesis of a modified urf13-T protein having a sensitivity-loss modification, i.e., that fails to confer toxin sensitivity on the organism expressing it. It is important that, while more than one toxin sensitivity domain exists in the urf13-T protein, a total loss of the toxin sensitivity function is achievable by a modification of a single domain. It is possible that not every modification within a toxin sensitivity domain will result in a sensitivity-loss modification. A toxin-sensitivity domain is variable in size, with an upper limit of about 10% or less of urf13-T, or coding for not more than 12 amino acids. The urf13-T gene can be modified at more than one toxin sensitivity domain to reduce the probability of subsequent reversion to toxin sensitivity in a host organism. The probability of two independent reversions occurring in a doubly modified protein is the product of the individual probabilities of reversion at each of the modified domains.

The method of measuring the effects of specific modifications of the urf13-T gene includes cloning the modified gene in a suitable plasmid expression vector, expressing the modified gene in a host microorganism and measuring the $O_2$ consumption and/or ion leakage of the host microorganism in the presence and absence of BmT or methomyl or toxin analogs thereof. The modifications may be nucleotide base changes, sequence deletions, sequence insertions, frame shifts or the like as understood by those skilled in the art. The techniques for introducing such modifications are known to those of ordinary skill in the art.

A modified urf13-T protein that lacks the function of conferring toxin sensitivity to a host organism that expresses it is termed a toxin-insensitive urf13-T protein herein abbreviated TI-urf13-T protein. Its modified gene is hence a TI-urf13-T gene. The designation, TI-urf13-T gene, specifically refers to a gene bearing a sensitivity-loss modification. The fact that discrete toxin sensitivity domains have been discovered indicates that the loss of toxin sensitivity is not the result of a general, nonspecific disruption of protein structure or conformation. TI-urf13-T proteins continue to be localized in the microorganism host cell membrane. Loss of toxin sensitivity therefore does not necessarily lead to loss of other functions. A modified urf13-T gene that yields toxin-sensitivity is deemed equivalent to unmodified urf13-T and is not separately designated, but simply referred to as an urf13-T gene herein.

A TI-urf13-T gene can be used to develop host cells and mitochondria that lack toxin sensitivity but otherwise possess the characteristics that result in male sterility, under appropriate developmental conditions. The male sterility phenotype is not manifested by currently-known characteristics of single cells. It is not known whether the urf13-T protein causes male sterility. Although it is uniquely expressed by T-mitochondria, its origin appears to be the result of several gene rearrangements (Dewey et al. (1985), Dewey et al. (1987)). Other effects that are the consequence of these rearrangements may be responsible for, or contribute to, the cms phenotype. Further understanding of the interaction of the urf13-T gene and its expression product with the components of the respiratory system of mitochondria or microorganisms will provide a basis for utilizing TI-urf13-T in plants to produce toxin-insensitive male sterility.

Using the disclosed method for evaluating the ability to confer toxin sensitivity makes it possible to map the urf13-T gene to locate domains responsible for toxin sensitivity. The gene can be modified by any of a variety of mutagenic techniques known in the art. Site-specific mutagenesis is a preferred method, using a series of mismatch oligonucleotide primers for introducing nucleotide sequence variations at any desired locus within the gene. The exact sequence change produced by such means can be identified by nucleotide sequence determination in the region affected by the change. A modified gene can be tested for functional effect of the modification by cloning the gene in an expression vector, as previously disclosed herein, or using an expression system known in the art, and expressing the modified gene in a microorganism transformed thereby. If the transformed microorganism expressing the modified gene is sensitive to toxin at a level comparable to the same organism expressing unmodified urf13-T, the modified gene is classified as "sensitive," indicating that the modified protein expressed thereby confers toxin sensitivity on the microorganism expressing it. If the microorganism is not toxin sensitive (after control experiments demonstrate that the modified protein is made and localized in the microorganism membrane) the modified gene is classed as "insensitive." Membrane localization is measured by binding of dicyclohexylcarbodiimide (DCCD). The fact that DCCD only binds to specific residues of proteins in hydrophobic environments provides a convenient assay for the intracellular location of proteins encoded by modified urf-13-T genes. The use of $^{14}$C-labeled DCCD provides a straightforward assay for monitoring the binding of DCCD to the protein. Only when the protein is inserted into a membrane will the labeled DCCD become covalently bound to it.

The described procedure has been used to identify three domains wherein modifications lead to insensitive (TI-urf13-T) genes: 1) Deletion of amino acids 2 through 11 results in insensitivity. There is therefore a toxin sensitivity domain within the sequence of amino acids 2 through 11. 2) A toxin sensitivity domain beginning at amino acid 83 exists. Deletion of carboxy-terminal amino acids from 84 to the carboxy end has no effect on toxin sensitivity. However, conversion of the codon for amino acid 83 to a termination (stop) codon results in a toxin-insensitive protein. Thus, a critical length for toxin sensitivity is defined by amino acid 83. Amino acid 83 is required for toxin-sensitivity under certain conditions. The domain comprising amino acid 83 extends from there toward the carboxy terminus of the protein. 3) A third toxin sensitivity domain comprising amino acid 39 has also been discovered. Mutation of the coding sequence for the amino acid at position 39 (an aspartic acid residue in the wild-type version of the protein) to code for either histidine glutamic acid, valine or alanine results in a toxin-insensitive protein. The conversion to toxin-insensitivity by the conservative replacement with glutamic acid (i.e., an acidic residue replacing an acidic residue) is surprising, and it indicates that the presence of an aspartic acid residue at position 39 in the 115 amino acid protein is essential for conferring toxin sensitivity. All domains are independent in the sense that a sensitivity-loss modification in any domain alone is sufficient to confer toxin insensitivity.

It will be apparent to those of ordinary skill in the art that additional mutations can be tested and a complete map of all toxin sensitivity domains obtained if desired, so that those of ordinary skill can generate TI-urf13-T genes following the teachings herein, without undue experimentation. Further, it will be apparent that one can find the minimum modifications, perhaps even single base changes, within each toxin sensitivity domain that result in toxin insensitivity. One can also construct a doubly modified gene that has modifications in more than one toxin sensitivity domain. The probability of reversion to toxin sensitivity is thereby reduced by several orders of magnitude.

Expression of a TI-urf13-T gene leads to synthesis of a TI-urf13-T protein. Expression vectors are well-known in the art. Choice of expression vector is a matter of the exercise of ordinary skill in the art, taking into consideration the characteristics of the expression system and the desired means of inducing protein synthesis. Two vectors for expression in E. coli have been used in the experiments described in the examples. Using the pATH vector, the urf13-T gene or its modified counterparts is expressed under the trpE promoter control. Another preferred vector termed PLC236, uses the lambda $P_L$ promoter, regulated by a temperature sensitivity repressor (pPLC36, Remaut, E. (1981) Gene 15:81). Use of the $P_L$ vector is recommended for expression in E. coli because the induction is accomplished by a temperature shift. Publicly-available vectors are also suitable for expressing urf13-T, for example, the pPOP series, the pLG series (200, 338, 339 and 400) the pKT series (279, 280, 287) and lambda gt11, all available from the American Type Culture Collection, 12301 Parklawn Drive, Rockville, Md. U.S.A.

Modified TI-urf13-T proteins are synthesized by cells expressing the modified gene. The proteins can be isolated and purified if desired using techniques previously disclosed by Dewey et al. (1987). The reference disclosed antibodies specific for urf13-T protein. One such antibody was raised against an oligopeptide composed of amino acids 92 through 106, designated PEP 13 therein. Another antigenic peptide has been disclosed by Wise, R. P. et al. (1987) Plant Mol. Biol. 9:121, together with an antibody thereto. Designated PEP 17, the epitope is composed of the urf13-T sequence of amino acids 32–48. Modified TI-urf13-T peptides that possess either sequence, for example, peptides modified in a toxin-sensitivity domain of amino acids 2 through 11, react with either antibody. The antibody can be used to assay such TI-urf13-T proteins or it can be used for purification by affinity chromatography. Similar antibodies can be raised by those of ordinary skill in the art for assaying and purifying the TI-urf13-T protein modified in the amino acids 83 through 85 domain. While the disclosed TI-urf13-T protein modified in domain 83 through 85 lacks amino acids 83 through 115, other proteins modified in the same domain can be full length and can be assayed by the same PEP 13 antibody disclosed previously by Dewey et al. (1987).

Both TI-urf13-T and urf13-T proteins can also be identified through their binding to $^{14}$C-labeled DCCD. Membrane preparations containing these proteins are incubated with the labeled DCCD, and the proteins are subsequently visualized by fluorography, an exercise of ordinary skill in the art.

The invention is further disclosed in the following examples. The examples show how the urf13-T gene was cloned in an expression vector, introduced into *E. coli* and expressed in *E. coli*. The effects of BmT and methomyl on transformed *E. coli* were tested. Modified urf13-T genes were constructed and their activity in a toxin-sensitivity assay tested. Toxin-sensitivity domains were identified, as described. Because the physiological effect of urf13-T protein in *E. coli* is the same as in maize with respect to toxin sensitivity, it is evident that any microorganism with a respiratory system will respond similarly. Therefore the procedure described in the examples can be repeated for other microorganisms without difficulty by those of ordinary skill in the art. Modifications that optimize the procedures for other organisms, choice of media, growth conditions, choice of expression vector, transformation protocols and the like are readily available and understood by the person of ordinary skill.

Except as noted hereafter, standard techniques for cloning, DNA isolation, amplification and purification, for enzymatic reactions involving DNA ligase, DNA polymerase, restriction endonucleases and the like, and various separation techniques, are those known and commonly employed by those skilled in the art. A number of standard techniques are described in: Maniatis et al. (1982) Molecular Cloning, Cold Spring Harbor Laboratory, Cold Spring Harbor, N.Y.; Wu (ed.) (1979) Methods Enzymol. 68; Wu et al. (eds.) (1983) Methods Enzymol. 100 and 101; Grossman and Moldave (eds.) Methods Enzymol. 65; Miller (ed.) (1972) Experiments in Molecular Genetics, Cold Spring Harbor Laboratory, Cold Spring Harbor, N.Y.; Old and Primrose (1981) Principles of Gene Manipulation, University of California Press, Berkeley; Schleif and Wensink (1982) *Practical Methods in Molecular Biology;* Glover (ed.) (1985) *DNA Cloning* Vols. I and II, IRL Press, Oxford, UK; Hames and Higgins (eds.) (1985) *Nucleic Acid Hybridisation,* IRL Press, Oxford, UK; and Setlow and Hollander (1979) *Genetic Engineering: Principles and Methods,* Vols. 1–4, Plenum Press, New York, which are incorporated by reference herein. Abbreviations, where employed, are those deemed standard in the field and commonly used in professional journals such as those cited herein.

EXAMPLES

Example 1

The entire urf13-T gene was cloned into the plasmid vector pATH 3 and expressed in *E. coli* strain JM109 (Yanish-Perran, C. et al. (1985) Gene 33:103) ATCC accession no. 53323, as described.

The pATH13-T plasmid was constructed using the pATH3 expression vector, the urf13-T gene of cms-T mitochondria, and two complementary synthetic oligonucleotides. The urf13-T gene contains two BclI restriction sites, one of which cuts at the putative initiator methionine codon. Digestion of the clone containing urf13-T with the restriction endonuclease HindIII, followed by a partial digestion with BclI enabled us to obtain a fragment that contained the entire urf13-T gene except for the first two nucleotides of the ATG initiation codon (plus approximately 450 base pairs of 3' flanking region). The pATH 3 plasmid was linearized by cleavage of the EcoRI and HindIII sites located within the polycloning region of the vector. Two complementary oligonucleotides corresponding to the sequences 5'-AATTCTGGAGGAAAAAATTAT-3' (SEQ ID NO.1) (top strand) and 5'-GATCATAATTTTTTCCTCCAG-3' (SEQ ID NO.2) (bottom strand) were annealed to yield a fragment with EcoRI and BclI sticky ends. The linear pATH 3 vector and the BclI-HindIII fragment containing urf13-T were joined by ligation of the EcoRI end of pATH 3 to the EcoRI end of the oligomer fragment, ligation of the BclI end of the oligomer fragment to the BclI end of the urf13-T sequence, and ligation of the HindIII end of the urf13-T fragment to the HindIII end of pATH 3. The oligonucleotides were constructed to provide a procaryotic ribosome binding site and to reconstitute the initiator ATG codon of urf13-T. The integrity of the pATH13-T construct was verified by nucleotide sequence analysis. The oligonucleotides were prepared with the Applied Biosystems 380A DNA Synthesizer according to the manufacturer's instructions. Cloning procedures were conducted as described by T. Maniatis, E. F. Fritsch, J. Sambrook, in *Molecular Cloning, A Laboratory Manual* (Cold Spring Harbor Laboratory, Cold Spring Harbor, N.Y., 1982). The structure of the pATH 3 expression vector and conditions of transcriptional induction of the trp promoter were according to Spindler, K. R. Rosser, D. S. E. Berk, A. J. (1984) J. Virol. 49:132, with modifications described by T. J. Koerner (personal communication). Optimal expression of the urf13-T in the pATH13-T vector was obtained in an M9 medium with amino acids minus tryptophan, glucose and thiamine. Although the pATH 3 expression vector was designed to enable synthesis of trp E fusion proteins (see, e.g., Dickmani et al. (1985) J. Biol. Chem. 260:1513), the pATH13-T plasmid was constructed so that the urf13-T sequence was out of frame with the trpE reading frame allowing production of an unfused 13 kD protein.

The pATH 3 - urf13-T construct, designated pATH13-T is transcriptionally regulated by the trpE promoter of E. coli and produces a 13 kD protein upon induction. This polypeptide co-migrates electrophoretically with the mitochondrial urf13-T protein product of cms-T maize on SDS-polyacrylamide gels as determined by protein blot analysis. Nucleotide sequence analysis confirmed that the urf13-T reading frame in pATH13-T was identical with the maize reading frame (data not shown). Although identical in nucleotide sequence, a difference in amino acid composition of the pATH13-T and urf13-T proteins may exist due to a possible difference in codon usage.

A modified urf13-T gene that produces a form of the 13 kD protein missing amino acids 2 through 11 was also constructed and expressed in E. coli using the plasmid vector pJG200.

A BclI-BglII fragment (positions 1248 to 1723 according to Dewey et al. containing all of the urf13-T reading frame except for the first 11 codons (along with approximately 150 base pairs of 3' flanking sequence) was ligated into the BamHI site of the expression vector pJG200. Since plasmid pJG200 utilizes the initiator methionine codon of the lambda cro gene, the resulting construct (pJG13-T) encoded all of the urf13-T reading frame except codons 2 through 11. The pGJG200 vector and conditions for induction of transcription are described by Germino, J. et al. (1983) Proc. Natl. Acad. Sci. U.S.A. 80:6848, and Germino, J. and Bastia, D. (1984) Proc. Natl. Acad. Sci. U.S.A. 81:4692.

The truncated urf13-T - pJG200 construct, designated pJG13-T, is under thermoinducible control of the cI857 thermolabile repressor and Pr promoter of phage lambda. E. coli cells containing plasmid pJG13-T abundantly expressed the modified form of the 13 kD protein after temperature induction at 42° C. Although the pJG13-T protein product was 10 amino acids shorter than the 13 kD protein produced by the pATH13-T plasmid or the urf13-T gene of cms-T mitochondria, no difference in electrophoretic mobility was detected by protein blotting.

The truncated protein, like the intact 13 kD polypeptide, is localized in the membrane of E. coli (data not shown).

Another expression vector, pLC236 (Remaut, E. (1981)) has been used successfully for expressing the urf13-T gene in modifications thereof. Expression is controlled by the lambda $P_L$ promoter and the promoter is thermoinducible. Use of pLC236 is deemed the best of the three vectors exemplified, because of the high expression levels and ease of induction. After introducing mutations in the urf13-T gene the mutant sequences (attached to prokaryotic translation signals) were inserted into the pLC236 vector and transformed into an E. coli host carrying the cI857 gene that produces a temperature-sensitive repressor protein.

Example 2

The effects have been measured of the BmT-toxin and methomyl on respiration in E. coli cells containing the pATH13-T and pJG13-T plasmids that have been induced to express the normal and truncated 13 kD proteins, respectively.

Additions of 780 ng/ml BmT-toxin and/or 4 mM methomyl were made to E. coli cultures expressing the plasmids pATH3, pATH13-T, and pJG13-T. The reaction medium contained 42 mM $Na_2HPO_4$, 22 mM $KH_2PO_4$, 8.5 mM NaCl, 19 mM $NH_4Cl$, 10 mM glucose and from 150 to 200 µg E. coli protein. $O_2$ consumption was measured polarographically with a Clark oxygen electrode. Respiration rates were expressed as nmol $O_2$ consumed/min/mg E. coli protein.

$O_2$ consumption was completely inhibited by the addition of 780 ng/ml BmT-toxin or 4 mM methomyl in cells producing the complete 13 kD protein. Respiration was not altered by toxin or methomyl in control cells transformed with the pATH 3 vector containing no insert, or in the cells producing the truncated version of the 13 kD protein.

The time required to completely inhibit respiration after toxin addition in E. coli cells was dependent on the concentration of the toxin. Although $O_2$ consumption was completely inhibited at toxin concentrations of 7.8 ng/ml, eight to nine minutes were required for full inhibition. In contrast, complete inhibition was achieved after approximately one minute with 780 ng/ml of toxin.

Example 3

In cms-T mitochondria, BmT-toxin and methomyl cause a rapid decrease in $A_{520}$ that has been interpreted as mitochondrial swelling (Miller, R. J. et al. (1971) Science 173:67; Koeppe, D. E. et al. (1978) Science 210:1227; Berville, A. et al. (1984) Plant Physiol. 76:508; Klein, R. R. et al. (1985) Plant Physiol. 77:912). To determine whether E. coli cells synthesizing the 13 kD protein showed similar effects, changes in absorbance were recorded for spheroplasts from pATH13-T induced E. coli cells in the presence of toxin and methomyl.

E. coli cells expressing the plasmids pATH 3 and pATH13-T were treated with 780 ng/ml toxin and 4 mM methomyl. E. coli spheroplasts were prepared as previously outlined (Burstein, C. et al. (1979) Eur. J. Biochem. 94:387). Absorbance measurements were made spectrophotometrically in a medium containing 10 mM Tris-HCl pH 8.0, 30% sucrose, 10 mM EDTA, 10 mM glucose, and from 0.45 to 0.6 mg of E. coli protein.

BmT-toxin and methomyl induced dramatic swelling in E. coli spheroplasts that produced the 13 kD polypeptide; no effect was seen with spheroplasts containing the pATH 3 control plasmid. In accord with the respiration results, E. coli spheroplasts producing the truncated 13 kD protein from plasmid pJG13-T showed no stimulation in swelling after the addition of toxin or methomyl.

To determine the effect of the BmT-toxin on E. coli growth, the $A_{550}$ of pATH13-T induced cell cultures was monitored for several hours both in the presence and absence of toxin. No growth was detected in E. coli cultures (log phase) expressing the 13 kD polypeptide during a six hour period after addition of BmT-toxin (780 ng/ml), whereas the same cells without toxin exhibited growth rates similar to cells containing the pATH 3 control plasmid.

Example 4

The effects of BmT toxin on ion-leakage in E. coli cells expressing urf13-T and TI-urf13-T genes have been measured.

Four different cultures of *E. coli* were used: 1) "Control," containing a pLC236 plasmid with no insert, 2) "T-urf13," containing a pLC236 plasmid with the full-length urf13-T gene inserted, 3) "92 aa," containing a pLC236 plasmid with a truncated urf13-T gene coding for the first 92 amino acids of the 13 KDa urf13-T protein, and 4) "82aa," containing a pLC236 plasmid with a truncated urf13-T gene coding for the first 82 amino acids of the urf13-T protein.

All four cultures were incubated for 30 minutes in the presence of $^{86}$Rb to allow energy-dependent uptake of the isotope (as described in Braun et al. (1989) in *The Molecular Basis of Plant Development*, 92: 79–85. All four cultures responded similarly, accumulating comparable amounts of $^{86}$Rb. BmT toxin, at a concentration of 1 $\mu$M, was added to each culture after 30 minutes. The cultures expressing the full-length urf13-T protein or the 92 amino acid (truncated) urf13-T protein were severely affected by addition of the toxin, showing rapid loss of the $^{86}$Rb ions from the cells within the first minute of exposure to toxin. In contrast, the control culture and the culture expressing the 82 amino acid (truncated) urf13-T protein showed no leakage of ions from the cells upon exposure to toxin.

Example 5

Various modifications of the urf13-T gene have been tested for their effects on the toxin sensitivity conferred by expression of the urf13-T gene itself. The modifications were made using known techniques of site-directed mutagenesis, using mismatch oligonucleotide primers. The efficiency of recovery of mutants was enhanced using the technique of Kunkel, T. (1985) Proc. Natl. Acad. Sci. U.S.A. 82:488. The nature of the nucleotide sequence change produced in the mutant was confirmed directly by sequence analysis over the region modified. The modified genes were then expressed essentially as described in Example 1. Strains expressing the modified genes were tested for BmT and methomyl sensitivity as described in Example 2. Results are tabulated in Table 1. Where the modification had no effect (produced the same level of toxin sensitivity as unmodified urf13-T) the result was scored as "sensitive." When the modification yielded an organism that lacked toxin sensitivity, it was scored as "insensitive." Three domains were identified when a modification resulted in a loss of toxin sensitivity. Near the —NH$_2$ end, amino acids 2 through 11 were seen to be essential for toxin sensitivity. The presence of amino acid 83 was also essential for toxin sensitivity. Deletion of the entire —COOH terminus from amino acids 84 through 115 had no effect on toxin sensitivity. However, insertion of a stop codon at position 83 resulted in toxin insensitivity. An internal deletion that eliminates the leucine residue at position 83, leading to a protein 114 amino acids in length, results in a toxin-sensitive protein. Therefore, a critical length of 83 amino acids is required for toxin sensitivity. The amino acid at position 39 is also essential for toxin sensitivity. If the DNA sequence is modified so that the amino acid at position 39 is histidine, glutamate, valine or alanine, the protein is toxin-insensitive. Thus, the presence of an aspartate moiety at position 39 is essential to toxin sensitivity of the 115 amino acid urf13-T protein. Modifications that result in a different amino acid being present at position 39 in the 115 amino acid protein will produce a toxin-insensitive protein.

Additionally, certain mutations at positions 56 or 67, which substituted a basic amino acid (lysine) for an acidic amino acid, dramatically affected the quantity of protein accumulated in the cells. This indicates that the introduction of positively charged amino acids between positions 55 and 68 lead to instability of the resulting protein.

From the foregoing it will be apparent that other modifications than those disclosed herein can lead to construction of TI-urf13-T genes, and synthesis of other TI-urf13-T proteins having other sorts of nucleotide sequence modifications than the ones disclosed herein. Such modifications can be made within the domains identified above that are essential for toxin sensitivity. Modifications within those domains need not involve all amino acids within the domain and may indeed require only a single amino acid change within the domain to produce the toxin insensitivity phenotype. Furthermore, it will be understood that silent mutations within the toxin sensitivity domains can be made, i.e., those that do not result in loss of toxin sensitivity. Instances of silent mutations are shown in Table 1. Furthermore, it will be readily apparent that the teachings and disclosures herein, as well as other teachings known in the art, make further mapping of the urf13-T gene and identification of other toxin sensitivity domains if they exist, a matter of routine. All such modifications and mutations that yield a TI-urf13-T gene or a TI-urf13-T protein therefore lie within the scope of the present invention.

TABLE 1

The effect of specific amino acid changes in urf13 on the sensitivity of *E. coli* to the T-toxin.

| Amino acid number(s) | Original Residue | Mutant Residue | Toxin Effect |
|---|---|---|---|
| 2–11 | Ile—Thr—Thr—Phe—Leu—Asn—Leu—Pro—Pro—Phe (SEQ ID NO.3) | deleted | insensitive |
| 2 | Ile | deleted | sensitive |
| 2 | Ile | Asn | sensitive |
| 2 | Ile | Ser | sensitive |
| 8 | Leu | Arg | sensitive |
| 8 | Leu | His | sensitive |
| 9 | Pro | Arg | sensitive |
| 9 | Pro | His | sensitive |
| 9 | Pro | Leu | sensitive |
| 10 | Pro | Arg | sensitive |
| 10 | Pro | His | sensitive |
| 10 | Pro | Leu | sensitive |
| 12 | Asp | Glu | sensitive |
| 12 | Asp | Arg | sensitive |
| 12 | Asp | Gly | sensitive |
| 12 | Asp | His | sensitive |
| 12 | Asp | Ala | sensitive |
| 12 | Asp | Val | sensitive |
| 12;39 | Asp;Asp | Val;Ala | insensitive |
| 12;39–40 | Asp;Asp—Asp | Gly;Ala—His | insensitive |
| 12;40 | Asp;Asp | Gly;His | sensitive |
| 12;48 | Asp;Glu | Arg;Gln | sensitive |
| 12;67 | Asp;Glu | Arg;Gln | sensitive |
| 27 | Cys | Ser | sensitive |
| 27 | Cys | Pro | sensitive |
| 39 | Asp | Glu | insensitive |
| 39 | Asp | His | insensitive |
| 39 | Asp | Val | insensitive |
| 39–40 | Asp—Asp | Ala;His | insensitive |
| 40 | Asp | His | sensitive |
| 40 | Asp | Tyr | sensitive |
| 48 | Glu | Gln | sensitive |

TABLE 1-continued

The effect of specific amino acid changes in urf13 on the sensitivity of *E. coli* to the T-toxin.

| Amino acid number(s) | Original Residue | Mutant Residue | Toxin Effect |
|---|---|---|---|
| 48 | Glu | Lys | sensitive |
| 56 | Glu | Gln | sensitive |
| 67 | Glu | Gln | sensitive |
| 72–73–74 | Trp—Leu—Arg | Ser—Gly-STOP | insensitive |
| 83 | Leu | deleted | sensitive |
| 83 | Leu | STOP | insensitive |
| 84 | Pro | STOP | sensitive |
| 85 | Ile | STOP | sensitive |
| 86 | Gln | STOP | sensitive |
| 88 | Asn | STOP | sensitive |
| 93 | Arg | STOP | sensitive |
| 102 | Lys | STOP | sensitive |

We claim:

1. A TI-urf13-T protein having a modified amino acid sequence as compared to the amino acid sequence of the native urf13-T protein, said modified sequence being characterized by at least one modification to a toxin sensitivity domain when compared with the native sequence of urf13-T protein wherein said modification comprises a deletion or substitution of at least one aminoacid, and whereby said modification results in a toxin insensitive protein.

2. The TI-urf13-T protein of claim 1, wherein the modification comprises modification of amino acid 39 of urf13-T protein.

3. The TI-urf13-T protein of claim 1 wherein the modification comprises at least one modification to the toxin sensitivity domain of amino acids 2 through 11 of urf13-T protein.

4. The TI-urf13-T protein of claim 1 wherein the modification comprises deletion of amino acids 2 through 11 of urf13-T protein.

5. The TI-urf13-T protein of claim 1 wherein the modification comprises modification of the toxin sensitivity domain beginning at amino acid 83 of urf13-T protein.

6. The TI-urf13-T protein of claim 1 wherein the modification comprises deletion of amino acids 83 through 115 of urf13-T protein.

7. The TI-urf13-T protein of claim 1 wherein the modification comprises substitution of any amino acid other than aspartate at position 39 of urf13-T protein.

8. The TI-urf13-T protein of claim 1 wherein the modification comprises substitution of glutamate, valine or alanine for the aspartate residue at position 39 of urf13-T protein.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

AATTCTGGAG GAAAAAATTA T                    21

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

GATCATAATT TTTTCCTCCA G                    21

( 2 ) INFORMATION FOR SEQ ID NO:3:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Ile  Thr  Thr  Phe  Leu  Asn  Leu  Pro  Pro  Phe
1                   5                        10
```